US00PP07826P

United States Patent [19]

Winchel

[11] Patent Number: Plant 7,826

[45] Date of Patent: Mar. 17, 1992

[54] ROSE PLANT NAMED "AGNES WINCHEL"

[76] Inventor: Joseph F. Winchel, 1605 Oakhorne Dr., Harbor City, Calif. 90710

[21] Appl. No.: 615,873

[22] Filed: Nov. 16, 1990

[51] Int. Cl.[5] ..... A01H 5/00

[52] U.S. Cl. ..... Plt./11

[58] Field of Search ..... Plt. 11-13

*Primary Examiner*—James R. Feyrer

[57] ABSTRACT

A new rose variety of the hybrid tea class characterized by having a multi colored bloom of deep pink edges blending to light pink center, almost white, on an upright bush with deep green foliage.

1 Drawing Sheet

BACKGROUND AND SUMMARY OF THE INVENTION

The present invention relates to a new and distinctive variety of rose plant of the hybrid tea class, which was originated by crossing "Dorothy Anne"×"Unnamed Seedling".

Among the novel characteristics possessed by the new variety which distinguish it from its parents and all other varieties of which I am aware of are:

(1) A deep pink border blending to the lightest of pinks.
(2) A vigorous upright plant of medium height.
(3) Exhibition form bloom.
(4) Rapid bloom repeat.

Asexual reproduction of the new rose variety by budding, as performed at Wasco, Calif. shows that the aforementioned characteristics and distinctions come true to form and as depicted in color as nearly true as it is reasonably possible to make the same in a color illustration of this character.

BRIEF DESCRIPTION OF THE DRAWING

The single sheet of the drawing depicts various parts of the new rose plant showing the characteristics and coloration of new and mature thorns and stems, foliage, buds in stages from newly formed to mature, flowers in progressive stages of opening in side and full face views, and a flower with petals removed to expose the calyx and stamens.

BOTANICAL DESCRIPTION OF THE PLANT

The following is a detailed description of the new variety with color terminology in accordance with the *Pantone Color Formula Guide* 747*XR*. The terminology used in the color description herein refers to plate numbers in the aforementioned color chart, e.g. "182U" is plate "182U" of the *Pantone Color Guide* 747*XR*.

American Rose Society Registration commercial appellation: "Agnes Winchel".
IRAR appellation: "Agnes Winchel."
Parentage: Seedling.
*Cross.*—"Dorothy Anne"×unnamed seedling.
Class: Hybrid tea.

The following observations are made of specimens grown outdoors in Los Angeles County, Calif. in the month of November.

FLOWER

Blooming Habit

A: Bud:
(1) *Size.*—Medium.
(2) *Form.*—Pointed.
(3) *Sepals.*—Usually 3.5-4 cm length with normal extension. Slight serration with no consistant number of appendages. No cotton. Color, close to 377U.
(4) *Peduncle.*—6-7 cm, strong and erect. Color, close to 484U, smooth surface.
(5) *Color when sepals first divide.*—Close to Rubine Red U.

B: Bloom:
(1) *Size.*—Medium 10 cm.
(2) *Borne.*—One to the stem.
(3) *Form.*—Classic exhibition, high centered.
(4) *Petalage.*—30-35.
(5) *Color.*—Outside petal border very edge close to 233U, fading towards the center to almost 230U with a center of creamy white with a tint of pink.

C: Petals:
(1) *Texture.*—Velvety.
(2) *Appearance.*—Inside velvety, outside satiny.
(3) *Form.*—Ovoid.
(4) *Arrangement.*—Wrapped.
(5) *Petaloids in center.*—Very few.
(6) *Persistance.*—Very good.
(7) *Fragrance.*—Slight fruity.
(8) *Lasting quality.*—Very good on bush and as cut flower.

REPRODUCTIVE ORGANS

A: Stamen:
(1) *Arrangement.*—Around pistil.
(2) *Number.*—Normal.
(3) *Length.*—Average.
(4) *Filament.*—Average.
(5) *Anthers.*—Color, close to 128U.
(6) *Pollen.*—Normal amount, yellow.

B: Pistil:
(1) *Styles.*—3-6 mm length, color, close to 193U.
(2) *Stigma.*—Color, close to 193U.
(3) *Ovary.*—Round.
(4) *Average maximum diameter.*—1 cm.
(5) *Average height.*—1 cm.

C: Hips: Will accept pollen.
(1) *Shape.*—Round.
(2) *Color.*—Orange when ripe.

(3) *Seed.*—10–15.

PLANT

A: Form: Upright, good growth habit.
B: Growth: Vigorous.
*Height.*—90–120 cm.
C: Foliage:
(1) *Size.*—Medium.
(2) *Quantity.*—Average, stems well covered.
(3) *Color.*—New foliage glossy, upper color, close to 209U; lower color, close to 209U. Mature foliage, upper color, close to 350C; lower color, close to 378U.
(4) *Shape.*—Oval with center pointed.
(5) *Texture.*—Upper side leathery and glossy, under side smooth and dull.
(6) *Edge.*—Scalloped.
(7) *Radius.*—60 cm.
D: Wood:

(1) *New wood.*—Color, close to 195U, smooth.
(2) *Mature wood.*—Color, close to 576U, smooth.
E: Thorns:
(1) *Color.*—Close to 483U.
F: Resistance to disease:
(1) *Mildew.*—Good.
(2) *Rust.*—Good.
(3) *Black spot.*—Good.
G: Winter hardiness: Good.

I claim:

1. A new and distinct variety of rose plant of the hybrid tea class, substantially as herein shown and described, characterized by its having deep pink shadings on outer petal edges fading to light pink, exhibition form, having a slight fragrance, firm and straight stem and a fast repeat blooming cycle, the plant is upright with glossy green foliage.

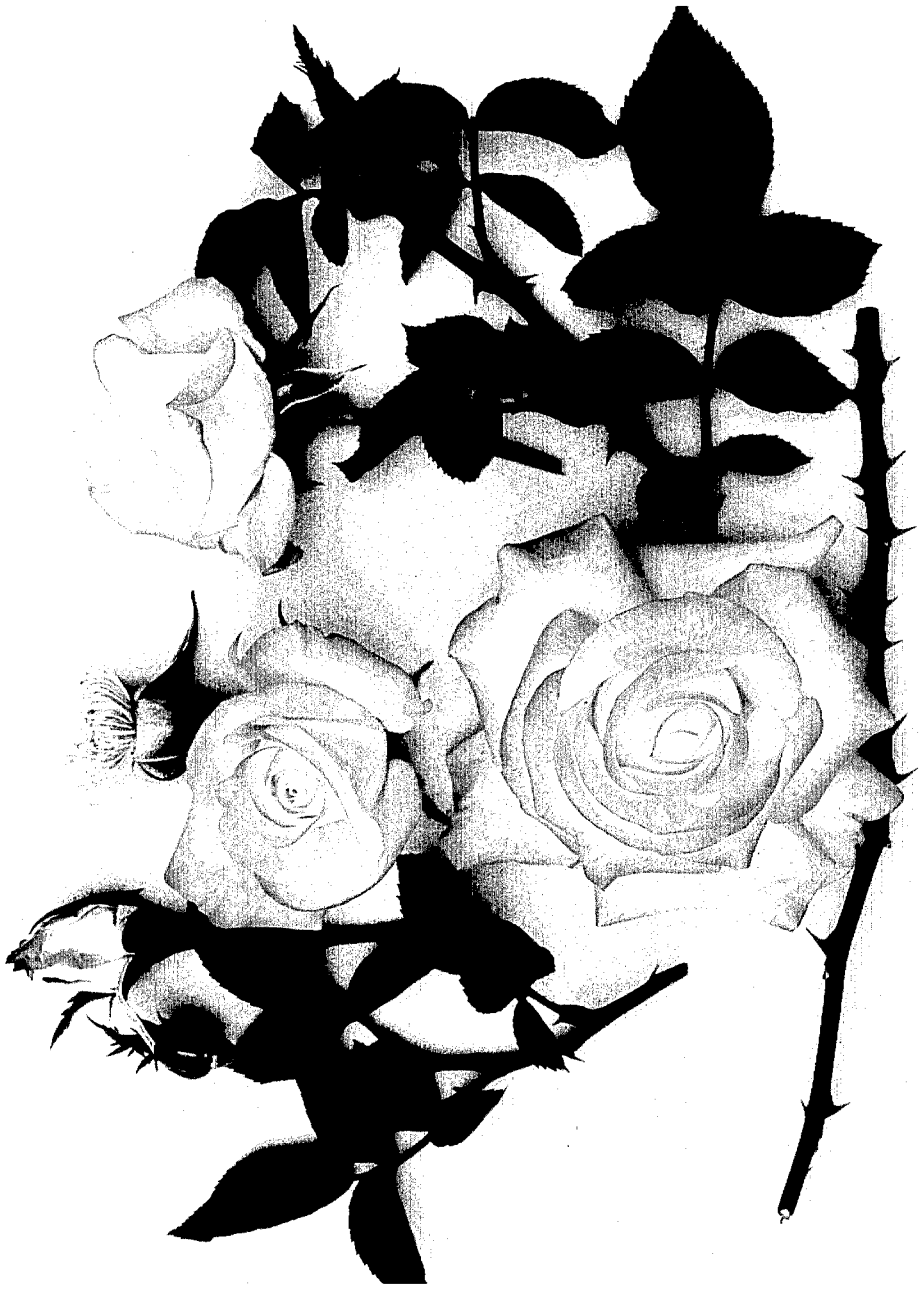

* * * * *